United States Patent [19]
Thaler et al.

[11] Patent Number: 5,608,029
[45] Date of Patent: Mar. 4, 1997

[54] MANNICH BASE POLYMERS

[75] Inventors: Warren A. Thaler, Flemington; Stephen Zushma, Clinton; Antonio Gutierrez, Mercerville, all of N.J.

[73] Assignee: Exxon Chemical Patents Inc., Linden, N.J.

[21] Appl. No.: 402,067

[22] Filed: Mar. 10, 1995

[51] Int. Cl.$^6$ .................................................. C08G 14/02
[52] U.S. Cl. ...................... 528/129; 528/137; 528/149; 528/162; 528/230; 528/266; 508/558
[58] Field of Search ...................... 528/230, 266, 528/129, 137, 149, 162; 252/50

[56] References Cited

U.S. PATENT DOCUMENTS

| | | | |
|---|---|---|---|
| 4,810,354 | 3/1989 | Roling et al. | 208/48 AA |
| 4,857,217 | 8/1989 | Gutierrez et al. | 252/47 |

OTHER PUBLICATIONS

Chemical Abstracts, vol. 120, No. 20, May 16, 1994, abstract No. 249113m Radchenko et al. "Oil for Hydraulic Systems of Industrial Machinery", p. 237.

"Preparation of Amphiphilic Polyisobutylenes–b–polyethylenamines by Mannich Reaction. III. Synthesis of Polyisobutylenes–b–polyethylenamines", Journal of Polymer Science, Part A, 31, pp. 1959–1966 (1993).

"Preparation of Amphiphilic Polyisobutylenes–b–polyethylenamines by Mannich Reaction. I. Synthesis and Characterization of α–Phenololigoisobutylenes", Journal of Polymer Science, Part A, 31, pp. 1923–1939 (1993).

"Preparation of Amphiphilic Polyisobutylenes–b–polyethylenamines by Mannich Reaction II. Study of Mannich Reaction on Model Systems", Journal of Polymer Science, Part A, 31, pp. 1941–1958 (1993).

*Primary Examiner*—Samuel A. Acquah
*Attorney, Agent, or Firm*—Estelle C. Bakun

[57] ABSTRACT

A process for producing an oil soluble interpolymer polymer of 1,2-alkylenediamine such as N-ethyl ethylenediamine, aldehyde-provider such as formaldehyde, and ortho-unsubstituted hydroxyaromatics such as 4-polyalkylene phenol is disclosed. The decyclized Mannich Base monomer units provide a higher viscosity material which is suitably substituted with a long chain hydrocarbyl para substituent such as polyisobutylene or ethylene/alpha-olefin polymer. Various ortho-substituted hydroxyaromatics such as o-cresol may be used to control the degree of polymerization. The polymers are useful as dispersants or other lubricant additives.

15 Claims, No Drawings

MANNICH BASE POLYMERS

BACKGROUND OF THE INVENTION

This invention relates to polymers derived from amines and hydroxy aromatic compounds, especially those suitable as Mannich Base dispersants, including conventional Mannich Base dispersants combined with such polymers. In the past, only the monomeric Mannich Base condensates have been available and these are limited to relatively low molecular weight/viscosity, except as adjusted by the size of the phenolic substituent, usually a polymer of 300–10,000 number average molecular weight (Mw). Journal of Polymer Science, Part A, 31, at pages 1955–1966 (1993) discloses a Mannich reaction of amines, formaldehyde, and phenols. Oil soluble hydroxyaromatic polymers are not taught. It has been found desirable to provide a polymeric Mannich Base additive whose viscosity/Mn can be adjusted by varying (especially limiting) the degree of polymerization rather than by changing the para substituent. The invention accomplishes this need and coincidentally, can also provide polymers with small or no para substituent which are useful as thickeners, viscosity agents, or antioxidants.

Various Mannich Base productions have suggested use of a broad range of components and conditions but none have been shown to produce the polymeric condensation adducts of the invention.

SUMMARY OF THE INVENTION

The invention is a process of forming an oil soluble hydroxyaromatic polymer comprising heating (i) a 1,2-alkylenediamine, a hydroxyaromatic compound having two open ortho positions, and more than an equivalent of aldehyde functional group from an aldehyde-providing compound, per equivalent of primary amine in the 1,2-alkylenediamine or (ii) their cyclized Mannich Base, and forming an oil soluble hydroxyaromatic polymer.

The invention is also a lubricant or additive concentrate comprising a synthetic lubricant and a polymer of a 1,2-alkylenediamine, a hydroxyaromatic compound having two open ortho positions, and an aldehyde-providing compound. The invention is also the above composition wherein said polymer has structural units of:

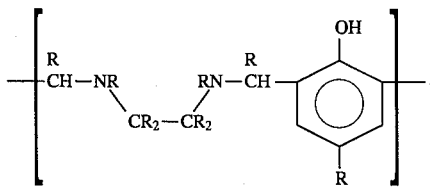

wherein each R is independently selected H or hydrocarbyl.

The invention is also a lubricant or additive concentrate comprising an oil soluble ring-opened polymer of:

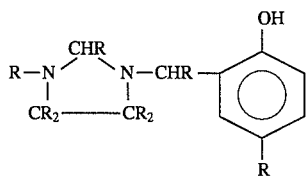

The invention is also a Mannich Base having the structure

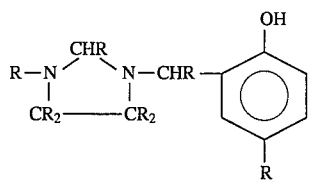

wherein the R's are independently selected H or hydrocarbonyl wherein the R on the para position of the aromatic ring has five or more carbon atoms.

The process of the invention provides sufficient amounts of oil soluble Mannich Base condensate polymers for use as lubricating oil additives. The polymers are characterized by the advantageous producibility of adjustable viscosity properties to permit ready handling. The polymers are also especially useful in a novel composition of synthetic lubricating oil or a blend of conventional and synthetic oils.

Various polymers of the invention having a small or no substituent para to the hydroxyl group of the hydroxyaromatic compound, are also usable as additives for antioxidant or other additive or Mannich Base use. Meta substituents are optional.

DESCRIPTION OF THE PREFERRED EMBODIMENTS

The process of the invention is suitable for providing sufficient portions of the condensation adduct polymers of the invention for use as dispersants and other additives.

According to the invention, polymers of Mannich Base condensation adducts are prepared from certain hydroxyaromatics, 1,2-alkylenediamines, and aldehyde-providers/producers.

The hydroxyaromatics usable in the invention are a broad class of aromatic compounds having at least one hydroxyl group or the equivalent and having two open ring positions adjacent to the hydroxyl(s), for a polymerization route. Thus the hydroxyaromatic compounds include those of structure

wherein Ar is phenyl, naphthenyl, anthracenyl, etc., such that b is usually 1, 2, or 3, conveniently 1 (phenyl), and a is one or more. Included are 1-naphthol, 2-naphthol, etc., hydroxyaromatics. These hydroxyaromatics have two open ortho positions for substitution in polymerization.

Suitable compounds include phenols, especially substituted phenols such as para-nitrophenol, para-alkylphenols preferably wherein the alkyl substituent is as or higher alkyl and other straight and branched chain alkyls and hydrocarbyls including (and preferably) polymers. The preferred polymer para substituents include polyalkenes such as polyisobutylene and ethylene/alpha-olefin interpolymers. The latter include ethylene/propylene and ethylene/butene copolymers. Copolymers of two alpha-olefins such as butene/propylene copolymer or a homopolymer such as atactic propylene, are also suitable ligands on the hydroxyaromatic compound. The meta positions are optionally substituted but such starting materials are not widely available. Such substituted hydroxyaromatics are suitable so long as the polymerization process is not prevented by their presence.

Other suitable hydroxyaromatics include the polyhydroxyl aromatics such as catechol, resorcinol, hydroquinone, and the polynuclear polyhydroxyls.

Also included are hydroxyl-equivalent aromatics such as bisphenols (diphenyl ethers). The above-mentioned substituents for phenols apply equally to the various polyhydroxyls and polynuclear aromatics.

The phenolic compounds are readily supplied by known routes. Phenols are alkylated with heating or using catalysts. Lower temperature alkylation, generally below 40° C. provides predominantly para-alkylated products whereas higher temperatures provide more ortho-substituted phenols and ortho-directing catalysts such as zeolites provide generally higher, up to about 60 percent ortho products. Solid acid catalysts often give about 50 percent ortho and 50 percent para-substituted products. For $BF_3$ alkylation of polyisobutylene onto phenol, lower temperature is generally used to avoid polymer degradation. Ethylene/alpha-olefin polymers are not so acid sensitive.

The non-ortho substituent of the hydroxyaromatic compound is preferably a polymeric substituent such as polyisobutylene or various other homopolymers including atactic polypropylene; or ethylene/alpha-olefin (EAO) interpolymers especially ethylene/propylene, ethylene/butene, and other copolymers. The EAO polymer substituents conveniently range from 20–80 molar percent ethylene with Mn of about 300–10,000, such as 700–5000 as commonly measured by GPC. The polymers are generally amorphous and oil soluble. In a preferred embodiment, the polymer substituent is derived from an EAO of at least about 30 percent terminal (preferably ethylidene) unsaturation. Such polymers are readily prepared from various metallocene catalyst systems as are well known in the art (typically with a methyl alumoxane cocatalyst).

The aldehyde-providing or aldehyde-producing entities of the invention include formaldehyde and its equivalents in various forms. These include paraformaldehyde, polyformaldehyde, aqueous formaldehyde, and trioxane. Other aldehyde group-containing compounds such as $C_2$–$C_{10}$ hydrocarbyl aldehydes (e.g., butyraldehyde, acetaldehyde, propionaldehyde, etc.) can also be employed. Preferred are those of the formula RCHO wherein R is H or $C_1$–$C_4$ hydrocarbyl.

The aldehyde providing compounds supply an "aldehyde,"

i.e., equivalents of aldehyde functional group for Mannich Base reaction and polymerization.

The 1,2-alkylene diamines of the invention have a primary amine by definition. These diamines may be polyamines, may have various substituents, especially hydrocarbyl including alkyl, and may be straight or branched chain diamines. They generally have the structure

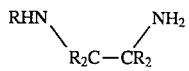

wherein the R's are hydrocarbyl, preferably alkyl, optionally with other substituents especially amino groups.

Thus, the R attached to the nitrogen may be nitrogen-containing hydrocarbyls. In other words, the above structure may represent polyamines such as diethylene triamine, triethylene tetramine, tetraethylene pentamine, pentaethylene hexamine and other polyethyleneamines and polyalkylene amines as well as other polyamines like $N_3$ (3 nitrogens) or higher polyamines optionally with varied substituents and groups linking nitrogen atoms.

In one embodiment of the invention, the R on the nitrogen may be a polymer substituent such as a PIB or EAO as described herein.

The 1,2-alkylene diamines include those of about 2 to 60, preferably 2 to 20 carbon atoms and about 2 to 12, preferably 2 to 9 nitrogen atoms in the molecule. These diamines may be hydrocarbyl amines which include other groups such as hydroxyls, alkoxys, amides, (?)nitriles, imidazolines, etc. Convenient amines include commercially available polyamines and any polyoxyalkylenes which are 1,2-alkylene diamines.

Non-limiting examples of suitable 1,2-alkylene diamines are polyethylene amines such as diethylene triamine, triethylene tetramine, tetraethylene, pentamine, polypropylene amines such as 1,2-propylene diamine, di-(1,2-propylene) triamine, and N-aminoalkyl piperazines having a 1,2-alkylene diamine terminus. N-alkyl ethylene diamine, including N-ethyl ethylenediamine, are a convenient class. Commercial products and mixtures of amines may be used. These include those sold under the trade names "Polyamine H", "Polyamine 400", and "Dow Polyamine E-100", as well as those heavy polyamines having an equivalent weight of about 120–160 grams per equivalent of primary amine and at least about 28 wt. percent nitrogen; alternatively having at least about seven (7) nitrogens per molecule and an equivalent weight of about 125–140 grams per equivalent of primary amine; alternatively having less than about 1 wt. percent pentamines and lower polyamines and less than about 25 wt. percent hexamines, optionally with substantially no oxygen. Amido amines such as those disclosed in U.S. Pat. No. 4,857,217 may be used.

Various common hydrocarbyl solvents are usable in the invention in suitable proportions to readily carry out the reaction. These solvents include heptane, n-propanol, pentane, hexane, butanol, etc. The 1,2-alkylene diamines and hydroxyaromatics undergo Mannich Base condensation according to the invention by providing more than an equivalent of aldehyde-providing compound per equivalent of primary amine in the 1,2-alkylene diamine. The additional portion of aldehyde (provider) permits and favors production of five-membered rings from 1,2-alkylene diamines. For example, N-alkyl 1,2-ethylenediamine condenses with two equivalents of formaldehyde and a para-hydrocarbylphenol to form:

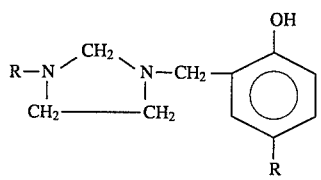

wherein R on the nitrogen is the alkyl group from the diamine and the R on the phenolic ring is the hydrocarbyl group from the phenolic reactant.

According to the invention, upon heating such compounds, the ring opens between the nitrogens and polymerizes to form polymers having the structural units

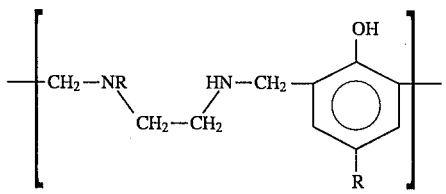

wherein the R's are as described above. Similarly, other aldehydes (providers) and hydroxyaromatics and 1,2-alkylenediamines form various polymers which may have other substituents. More equivalents of aldehyde functional groups are required for each additional primary amine in the 1,2-alkylenediamine to provide ring formation and, ultimately, polymerization as indicated. Also, with additional aldehyde, additional ring formation may be provided at two secondary amines separated by an ethylene or substituted ethylene linkage in polyamines. Such 5-membered rings in the polyamine may be opened on heating to condense with a hydroxyaromatic compound.

It is noted that those hydroxyaromatics not having two open ortho positions, while condensing with the five-membered ring from aldehyde and 1,2-alkylenediamine do not polymerize on heating.

Thus, e.g., the five-membered ring condensates with ortho cresol do not form polymer. This may, however, be used to advantage by proceeding with mixtures of hydroxyaromatics which permit polymerization and, selectively, a chain stopper of conventional type or an ortho-blocked hydroxyaromatic. Concurrently then, e.g., a portion of ortho-t-butyl phenol admixed with para-t-butyl phenol may be used to limit Mn and viscosity of the polymer.

Preferably about two (2) or more equivalents of aldehyde producer, preferably formaldehyde, are used per equivalent of primary amine to promote ring formation.

Heating is used either during the condensation, reaction to proceed to polymer in one step, or after condensation to open the 5-membered ring and form the polymer according to the invention.

Heating temperature to form the polymer of the invention varies according to the reactants used to form the condensate and thereby affecting the stability of the 5-membered ring. Generally, the heating temperature for most common condensates is about 150° C. or higher, preferably 160° C. or higher.

The polymers of the invention have a broad spectrum of utility in oleaginous compositions. Most notably, the polymers of the invention, either alone or in combination with Mannich Base or other dispersants, serve as dispersants/compositions for admixture with lubricants and fuels. The novel combination of the polymers of the invention with a synthetic oil or synlube composition is especially advantageous because such synthetic oil compositions require viscosity modification and such viscosity alteration is obtainable by proper selection of dispersant used in the oil. Moreover, by means of this invention, the viscosity alteration may be achieved by altering either the hydrocarbyl (alkyl, polymeric, etc.) substituent in the para (or comparable) position of the hydroxyaromatic compound or by regulating either the amount of aldehyde or amount of para-substituted hydroxyaromatic chain terminator.

The polymers and polymer Mannich Base mixtures of the invention are readily post treated such as by boration with boric acid boron oxide, boron halides, boron esters or other boron-attaching compounds, or by capping with known materials such as dodecycl succinic anhydride, maleic anhydride, polyisobutenyl/succinic anhydrides of varied molecular weights and other acylating agents. Such treatments tend to assure better interaction with elastomer/rubber seals which come into contact with the additives/dispersants/mixtures of the invention in oils.

The boration should be sufficient to provide from about 0.1 to 20 atomic proportions of boron for each mole of nitrogen composition. The borated dispersants of the invention usefully contain about 0.05 to 2.0 wt. percent boron. Treating is readily carried out by combining a slurry of boric acid to an oil solution of the dispersant at 135°–190° C. for 1 to 5 hours, followed by nitrogen stripping.

The polymers and mixtures of the invention can also be treated with polymerizable lactones such as epsilon caprolactone to form adducts. Similarly, the polymers and mixtures of the invention may be complexed with metal reactants such as metal nitrates, halides, phosphates, sulfates, borates, etc., of iron, cobalt, nickel, copper, chromium, etc.

The polymers, mixtures, and other additives of the invention are combined with oils and fuels in conventional manner or any convenient way including use of elevated temperature.

The polymers and mixtures of the present invention possess very good dispersant properties as measured herein in a wide variety of environments. Accordingly, the dispersants/additives are used by incorporation and dissolution into an oleaginous material such as fuels and lubricating oils. When the dispersants/additives of this invention are used in normally liquid petroleum fuels such as middle distillates boiling from about 65° to 430° C., including kerosene, diesel fuels, home heating fuel oil, jet fuels, etc., a concentration of the additives in the fuel in the range of typically from about 0.001 to about 0.5, and preferably 0.005 to about 0.15 weight percent, based on the total weight of the composition, will usually be employed.

The polymers and mixtures of the present invention find their primary utility in lubricating oil compositions which employ a base oil in which the additives redissolved or dispersed. Such base oils may be natural or synthetic. Base oils suitable for use in preparing the lubricating oil compositions of the present invention include those conventionally employed as crankcase lubricating oils for spark-ignited and compression-ignited internal combustion engines, such as automobile and truck engines, marine and railroad diesel engines, and the like. Advantageous results are also achieved by employing the polymers and mixtures of the present invention in base oils conventionally employed in and/or adapted for use as power transmitting fluids, universal tractor fluids and hydraulic fluids, heavy duty hydraulic fluids, power steering fluids and the like. Gear lubricants, industrial oils, pump oils and other lubricating oil compositions can also benefit from the incorporation therein of the polymers and mixtures of the present invention.

These lubricating oil formulations conventionally contain several different types of additives that will supply the characteristics that are required in the formulations. Among these types of additives are included viscosity index improvers, antioxidants, corrosion inhibitors, detergents, dispersants, pour point depressants, antiwear agents, friction modifiers, and other ashless dispersant (e.g., polyisobutenyl succinimides) and borated derivatives thereof), etc.

In the preparation of lubricating oil formulations it is common practice to introduce the additives in the form of 10 to 80 wt. %, e.g., 20 to 80 wt. % active ingredient concentrates in hydrocarbon oil, e.g. mineral lubricating oil, or other suitable solvent. Usually these concentrates may be diluted with 3 to 100, e.g., 5 to 40 pads by weight of lubricating oil, per part by weight of the additive package, in forming finished lubricants, e.g. crankcase motor oils. The purpose of concentrates, of course, is to make the handling of the various materials less difficult and awkward as well as to facilitate solution or dispersion in the final blend. Thus, a dispersant would be usually employed in the form of a 40 to 50 wt. % concentrate, for example, in a lubricating oil fraction.

The ashless dispersants of the present invention will be generally used in admixture with a lube oil basestock, comprising an oil of lubricating viscosity, including natural and synthetic lubricating oils and mixtures thereof.

Natural oils include animal oils and vegetable oils (e.g., castor, lard oil) liquid petroleum oils and hydrorefined, solvent-treated or acid-treated mineral lubricating oils of the paraffinic, naphthenic and mixed paraffinic-naphthenic types. Oils of lubricating viscosity derived from coal or shale are also useful base oils.

Alkylene oxide polymers and interpolymers and derivatives thereof where the terminal hydroxyl groups have been modified by esterification, etherification, etc., constitute another class of known synthetic lubricating oils. These are exemplified by polyoxyalkylene polymers prepared by polymerization of ethylene oxide or propylene oxide, the alkyl and aryl ethers of these polyoxyalkylene polymers (e.g., methyl-poly isopropylene glycol ether having an average molecular weight of 1000, diphenyl ether of poly-ethylene glycol having a molecular weight of 500–1000, diethyl ether of polypropylene glycol having a molecular weight of 1000–1500); and mono- and polycarboxylic esters thereof, for example, the acetic acid esters, mixed $C_3$–$C_8$ fatty acid esters and $C_{13}$ oxo acid diester of tetraethylene glycol.

Another suitable class of synthetic lubricating oils comprises the esters of dicarboxylic acids (e.g., phthalic acid, succinic acid, alkyl succinic acids and alkenyl succinic acids, maleic acid, azelaic acid, suberic acid, sebasic acid, fumaric acid, adipic acid, linoleic acid dimer, malonic acid, alkylmalonic acids, alkenyl malonic acids) with a variety of alcohols (e.g., butyl alcohol, hexyl alcohol, dodecyl alcohol, 2-ethylhexyl alcohol, ethylene glycol, diethylene glycol monoether, propylene glycol). Specific examples of these esters include dibutyl adipate, di(2-ethylhexyl)sebacate, di-n-hexyl fumarate, dioctyl sebacate, diisooctyl azelate, diisodecyl azelate, dioctyl phthalate, didecyl phthalate, dieicosyl sebacate, the 2-ethylhexyl diester of linoleic acid dimer, and the complex ester formed by reacting one mole of sebacic acid with two moles of tetraethylene glycol and two moles of 2-ethylhexanoic acid.

Esters useful as synthetic oils also include those made from $C_5$ to $C_{12}$ monocarboxylic acids and polyols and polyol ethers such as neopentyl glycol, trimethylolpropane, pentaerythritol, dipentaerythritol and tripentaerythritol.

Silicon-based oils such as the polyalkyl-, polyaryl-, polyalkoxy-, or polyaryloxysiloxane oils and silicate oils comprise another useful class of synthetic lubricants; they include tetraethyl silicate, tetraisopropyl silicate, tetra-(2-ethylhexyl)silicate, tetra-(4-methyl-2-ethylhexyl)silicate, tetra-(p-tert-butylphenyl)silicate, hexa-(4-methyl-2-pentoxy)disiloxane, poly(methyl)siloxanes and poly(methylphenyl)siloxanes. Other synthetic lubricating oils include liquid esters of phosphorus-containing acids (e.g., tricresyl phosphate, trioctyl phosphate, diethyl ester of decylphosphonic acid) and polymeric tetrahydrofurans.

Unrefined, refined and rerefined oils can be used in the lubricants of the present invention. Unrefined oils are those obtained directly from a natural or synthetic source without further purification treatment. For example, a shale oil obtained directly from retorting operations, a petroleum oil obtained directly from distillation or ester oil obtained directly from an esterification process and used without further treatment would be an unrefined oil. Refined oils are similar to the unrefined oils except they have been further treated in one or more purification steps to improve one or more properties. Many such purification techniques, such as distillation, solvent extraction, acid or base extraction, filtration and percolation are known to those skilled in the art. Rerefined oils are obtained by processes similar to those used to obtain refined oils applied to refined oils which have been already used in service. Such rerefined oils are also known as reclaimed or reprocessed oils and often are additionally processed by techniques for removal of spent additives and oil breakdown products.

Various other typical additive package components and individual additives are also usable in the compositions of the invention. These include metal-containing rust inhibitors and/or detergents such as metal salts of sulphonic acids, alkyl phenols, alkyl salicylates and other oil-soluble acids and highly basic metal salts and magnesium/calcium sulphonates or phenates; viscosity modifiers such as Mn of $10^4$–$10^6$ hydrocarbyl polymers/copolymers (ethylene/propylene) and polyester modifiers such as methacrylic acid, etc., antiwear agents such as dihydrocarbyl dithiophosphate metal salts like zinc salts; conventional or multifunctional antioxidants including copper salts; corrosion inhibitors such as phosphosulfuized hydrocarbon; oxidation inhibitors like alkylphenol thioesters; friction modifiers; pour point depressants; rust inhibitors; demulsifiers; and other compatible additives.

Thus additives for lubes such as two and four cycle additives, to improve engine cleanliness, can be prepared by Mannich base reaction of polymer alkylated phenols with more than 1 equivalent of aldehyde per equivalent of primary amino group in a polyethylene amine, and subsequently heating of the Mannich base intermediate to produce a polymeric product. Another aspect of this invention is to control the viscosity growth of the polymerized Mannich base by using either a mixture of ortho/para polymer alkylated phenol or using a mixture of phenol and cresol to produce the polymer alkylated phenol.

The higher the percentage of ortho blocked product, the lower the viscosity growth of the additive.

EXAMPLES

Example 1

The formation of a Mannich base according to the invention shown was produced by combining 4.06 g N-Ethyl ethylenediamine (2.4:1 ratio to primary amine), 6.90 g para-t-butyl phenol 3.36 g paraformaldehyde and 40 g heptane diluent, and heating for 3 hours at reflux (~80° C.). Carbon 13 nuclear magnetic resonance spectroscopy ("$^{13}$C NMR"), after removal of volatiles on a rotary evaporator, gave the structure:

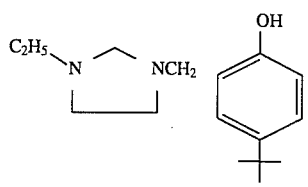

Attempted vacuum distillation of this liquid led to initial reflux in the still until the pot temperature reached about 160° C. whereupon the contents polymerized in an instant.

Solid state $^{13}C$ NMR displayed a ring opened structure consistent with the invention.

Example 2

Example 1 was repeated. After removal of solvent by means of a rotary evaporator, an attempt was made to distill the liquid product at high vacuum by means of a short path Kugelrohr apparatus.

Heating to 160° C. gave a small amount of solid in the collection bulb.

Analysis: C, 73.71; H, 9.48; N 9.22, O 8.30

The majority of the product polymerized in the distillation bulb.

Analysis: C, 75.10; H, 9.23; N, 7.03; 0.855.

Comparative Example 3

An ortho substituted phenol 2-tert-butyl-4-methyl phenol was substituted for the 4-t-butyl phenol of example 2.

A liquid Mannich base adduct was produced and showed a $^{13}C$ NMR consistent with the structure:

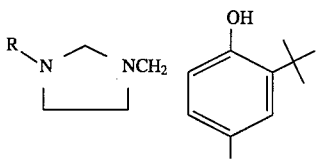

Short path distillation at about 140° C. at 0.05 mm showed that this product was distillable. Heating at 160° C. produced no polymer. Similar results are achieved with ortho-t-butyl phenol.

Thus, an ortho substituent blocks polymerization.

Example 4

Triethylene tetramine (TETA) 5.11 g; paracresol, 7.56 g; paraformaldehyde 5.18 g; Decane 1.52 g; and n-propanol 60.82 g were placed in a Parr pressure reactor and heated to 160° C. with stirring. Solid polymer was recovered.

Analysis: C, 69.05, 69.34; H 8.14, 8.15, O, 8.35,8.51; N, 12.29, 12.35.

Solid state $^{13}C$ NMR showed an opened ring polymer structure similar to example 1.

A series of experiments with phenol alkylated with copolymers of ethylene and butene-1, showed that the use of about 2 moles of formaldehyde per primary amine of commercial polyamine (PAM) "Dow E-100" gave Mannich base products which could show large increases in viscosity upon heating at elevated (>150° C.) temperatures. Interestingly, ortho/para alkylated phenol adducts showed significant viscosity growth upon heating but not nearly as severe as the viscosity increase from essentially all para alkylated phenol as shown below.

Example 5

This example illustrates the Mannich Base dispersant using 1.2 moles of formaldehyde per mole of primary amine when the intermediate is heated to 160° C. for 1 hour and the polymer alkylate comprises 30% ortho and 70% para. About 3148 grams (0.874 mol) of an ethylene/butene phenol alkylate (Mn=3600) was charged into a reactor and mixed with 99.6 grams of polyethylene amine (PAM) having 8.82 meq of primary amine per gram of PAM. The reactor mixture was heated to 90° C. and stirred under nitrogen atmosphere while adding 85.5 grams of formalin (37 percent aqueous solution of formaldehyde) over 25 minutes and then soaked at 90° C. for two hours. The reactor temperature was then increased to 165° C. and kept at this temperature for one hour and 2018 grams of mineral oil S150N were added. The viscosity of the Mannich Base intermediate was 717 cst at 100° C. The cool down product was kept at 140° C. and 289.4 grams of a 30% boric acid slurry was added over 15 minutes. The reactor temperature was increased to 160° C. and soaked for two hours. Then 1386 grams of mineral oil S100 neutral were added and the product was filtered. The 40% active ingredient solution analyzed for: 0.48% nitrogen with a viscosity of 3370 cst at 100° C.

Example 6

This example illustrates the Mannich Base dispersant using 2.0 moles of formaldehyde per mole of primary amine when the intermediate is heated to 160° C. for one hour and the polymer alkylate comprises 30% ortho and 70% para. About 3165 grams (0.88 mol) of an ethylene/butene phenol alkylate (Mn=3600) was charged into a reactor and mixed with 100.2 grams of polyethylene amine (PAM) having 8.82 meq of primary amine per gram of PAM. The reactor mixture was heated to 90° C. and stirred under nitrogen atmosphere while adding 143 grams of formalin (37 percent aqueous) over 25 minutes and then soaked at 90° C. for two hours. The reactor temperature was then increased to 165° C. and kept at this temperature for one hour and 2037 grams of mineral oil S150N were added. The viscosity of the Mannich Base intermediate was 783 cst at 100° C. The cool down product was kept at 140° C. and 291 grams of a 30% boric acid slurry was added over 15 minutes. The reactor temperature was increased to 160° C. and soaked for two hours. Then 2,395 grams of mineral oil S100 neutral were added and the product was filtered. The 35% active ingredient solution analyzed for: 0.40% nitrogen with a viscosity of 16,250 cst at 100° C.

Example 7

This example illustrates the Mannich Base dispersant using 1.2 moles of formaldehyde per mole of primary amine when the intermediate is heated to 160° C. for 4 hours and the polymer alkylate comprises 44% ortho and 56% para. About 3394 grams (1.04 mol) of an ethylene/butene phenol alkylate (Mn=3250) was charged into a reactor and mixed with 136.6 grams of polyethylene amine (PAM) having 8.82 meq of primary amine per gram of PAM. The reactor mixture was heated to 90° C. and stirred under nitrogen atmosphere while adding 117.2 grams of formalin over 25 minutes and then soaked at 90° C. for two hours. The reactor temperature was then increased to 165° C. and kept at this temperature for four hours and 2,169 grams of mineral oil S150N were added. The cool down product was kept at 140° C. and 396.7 grams of a 30% boric acid slurry was added over 15 minutes. The reactor temperature was increased to 160° C. and soaked for two hours. Then 1,519 grams of mineral oil S100 neutral were added and the product was filtered. The 40% active ingredient solution analyzed for: 0.57% nitrogen with a viscosity of 2420 cst at 100° C.

Example 8

This example illustrates the Mannich Base dispersant using 2.0 moles of formaldehyde per mole of primary amine when the intermediate is heated to 160° C. for 4 hours and the polymer alkylate comprises 44% ortho and 56% para. About 3199 grams (0.98 mol) of an ethylene/butene phenol alkylate (Mn=3250) was charged into a reactor and mixed with 127.8 grams of polyethylene amine (PAM) having 8.82 meq of primary amine per gram of PAM. The reactor mixture was heated to 90° C. and stirred under nitrogen atmosphere while adding 182.4 grams of formalin over 25 minutes and then soaked at 90° C. for two hours. The reactor temperature was then increased to 165° C. and kept at this temperature for four hours and 2,053 grams of mineral oil S150N were added. The cool down product was kept at 140° C. and 371.2 grams of a 30% boric acid slurry was added over 15 minutes. The reactor temperature was increased to 160° C. and soaked for two hours. Then 1,026 grams of mineral oil S 100 neutral were added and the product was filtered. The 40% active ingredient solution analyzed for: 0.52% nitrogen with a viscosity of 3370 cst at 100° C.

Example 9

This example illustrates the Mannich Base dispersant using 1.08 moles of formaldehyde per mole of primary amine when the intermediate is heated to 140° C. for 2 hours and the polymer alkylate comprises 54% ortho and 46% para. About 4.100 grams (0.0414 mol) of an ethylene/butene phenol alkylate (Mn=2016) was charged into a reactor and mixed with 4.8 grams of polyethylene amine (PAM) having 8.82 meq of primary amine per gram of PAM. The reactor mixture was heated to 90° C. and stirred under nitrogen atmosphere while adding 3.7 grams of formalin over 5 minutes and then soaked at 90° C. for two hours. The reactor temperature was then increased to 140° C. and kept at this temperature for four hours and 158 grams of mineral oil S150N were added. Then 2.73 grams of boric acid was added over 15 minutes. The reactor temperature was increased to 160° C. and soaked for two hours. The nitrogen stripped product was filtered. The product analyzed for 0.5 6% nitrogen with a viscosity of 166 cst at 100° C.

Example 10

This example illustrates the Mannich Base dispersant using 2.16 moles of formaldehyde per mole of primary amine when the intermediate is heated to 140° C. for 2 hours and the polymer alkylate comprises 54% ortho and 46% para. About 100 grams (0.0414 mol) of an ethylene/butene phenol alkylate (Mn=2016) was charged into a reactor and mixed with 4.8 grams of polyethylene amine (PAM) having 8.82 meq of primary amine per gram of PAM. The reactor mixture was heated to 90° C. and stirred under nitrogen atmosphere while adding 7.4 grams of formalin over 5 minutes and then soaked at 90° C. for two hours. The reactor temperature was then increased to 140° C. and kept at this temperature for four hours and 158 grams of mineral oil S150N were added. Then 2.73 grams of boric acid was added over 15 minutes, The reactor temperature was increased to 160° C. and soaked for two hours. The nitrogen stripped product was filtered. The product analyzed for: 0.5 6% nitrogen with a viscosity of 302 cst at 100° C.

Example 11

This example illustrates the Mannich Base dispersant using 1.1 moles of formaldehyde per mole of primary amine when the intermediate is heated to 145° C. for 2 hours and the polymer-phenol is primarily alkylated at the para position (91% para, 9% ortho). About 50 grams (0.022 mol) of an ethylene/butene phenol alkylate (Mn=2300) was charged into a reactor and mixed with 2.5 grams (0.022 eq. primary amine) of polyethylene amine (PAM) having 8.68 meq of primary amine per gram of PAM. The reactor mixture was heated to 90° C. and stirred under nitrogen atmosphere while adding 0.74 grams (0.0240 mol) of paraformaldehyde over half hour and then soaked at 90° C. for two hours. The reactor temperature was then increased to 145° C. and kept at this temperature for four hours and 57 grams of mineral oil S150N were added. Then 4.27 grams of a 30% boric acid oil slurry was added over 15 minutes. The reactor temperature was increased to 150° C. and soaked for two hours. The nitrogen stripped product was filtered. The product was analyzed for: 0.5 4% nitrogen with a viscosity of 230 cst at 100° C.

Example 12

This example illustrates the Mannich Base dispersant using 3.0 moles of formaldehyde per mole of primary amine when the intermediate is heated to 145° C. for 2 hours and the polymer-phenol is primarily alkylated at the para position (91% para, 9% ortho). About 50 grams (0.022 mol) of an ethylene butene phenol alkylate (Mn=2300) was charged into a reactor and mixed with 2.5 grams (0.022 eq. primary amine) of polyethylene amine (PAM) having 8.68 meq of primary amine per gram of PAM. The reactor mixture was heated to 90° C. and stirred under nitrogen atmosphere while adding 2.0 grams (0.066 mol) of paraformaldehyde over half hour and then soaked at 90° C. for two hours. The reactor temperature was then increased to 145° C. and kept at this temperature for four hours and 57 grams of mineral oil S150N were added. Then 4.27 grams of a 30% boric acid oil slurry was added over 15 minutes. The reactor temperature was increased to 150° C. and soaked for two hours. The product became very viscous while heating. It analyzed for 0.59% N. The viscosity could not be measured because the product in oil solution was too thick to measure at the bath temperature.

Example 13

The polymer of Example 11 replaces the conventional dispersant of an additive package in a passenger car motor oil formulation using polyalpha-olefin synthetic lubricating oil.

A reduced amount of viscosity modifier is necessary to provide appropriate viscosity at low and high engine temperatures.

Example 14

A synthetic lubricant is prepared as in Example 13 except that more than 95 wt. percent of the dispersant portion is a conventional Mannich Base dispersant and less than 5 wt. percent is the polymer of Example 11 to flexibly provide a slight increase in viscosity.

We claim:

1. A process of forming an oil soluble hydroxyaromatic polymer comprising heating (i) a 1,2-alkylenediamine; a hydroxyaromatic compound having two open ortho positions; and more than an equivalent of aldehyde functional group from an aldehyde-providing compound, per equivalent of primary amine in the 1,2-alkylenediamine or (ii) their cyclized Mannich Base; and forming an oil soluble hydroxyaromatic polymer.

2. The process of claim 1, wherein the heating is carried out at about 160° C. or higher.

3. The process of claim 1 with about 2 or more equivalents of aldehyde functional group per equivalent of primary amine.

4. The process of claim 1 wherein said aldehyde-providing compound is a formaldehyde.

5. The process of claim 1 wherein said 1,2-alkylene diamine is an $N_3$ or higher polyamine or polyethylene amine.

6. The process of claim 1 wherein polymerization is limited by the presence of an ortho substituted hydroxyaromatic.

7. An oil soluble polymer prepared by the process of claim 1, comprising a ring-opened polymer of a cyclized Mannich Base condensation adduct of a 1,2-alkylenediamine and a hydroxyaromatic compound.

8. An oil soluble polymer of claim 7, having structural units of:

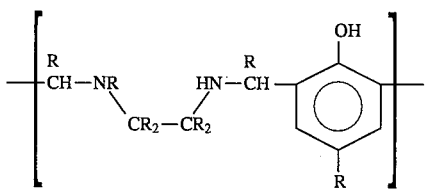

wherein each R is independently selected from the group consisting of H and hydrocarbyl.

9. A polymer of claim 7, wherein said hydroxyaromatic compound is a phenol having a para polymeric substituent.

10. A composition of a Mannich Base and at least about 5 wt. percent of a copolymer of claim 7.

11. A Mannich Base having the structure

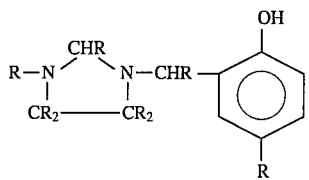

wherein the R's are independently selected from the group consisting of H and hydrocarbyl wherein the R on the para position of the aromatic ring has five or more carbon atoms.

12. The Mannich Base of claim 11 wherein the R on the para position of the aromatic ring is a polymer.

13. The ring-opened polymer of the Mannich Base of claim 11.

14. The polymer of claim 13 wherein the R on the nitrogen is a nitrogen containing hydrocarbyl group.

15. The Mannich Base of claim 11 derived from an $N_3$ or higher polyamine.

* * * * *